United States Patent [19]

Katz

[11] Patent Number: 4,642,096

[45] Date of Patent: Feb. 10, 1987

[54] POSITION LOCATING DEVICE AND METHOD FOR INTERSTITIAL RADIOTHERAPY

[76] Inventor: Harry R. Katz, 10121 Darmuid Green Dr., Potomac, Md. 20854

[21] Appl. No.: 626,333

[22] Filed: Jun. 29, 1984

[51] Int. Cl.⁴ ............................................. A61M 5/00
[52] U.S. Cl. ..................... 604/116; 128/DIG. 6; 128/303 B; 128/329 R; 128/346; 128/87 R
[58] Field of Search ................. 604/116; 128/1.1, 1.2, 128/303 B, 303 R, 329 A, 329 R, 346, DIG. 6, DIG. 15, DIG. 26, 87 R

[56] References Cited

U.S. PATENT DOCUMENTS

| | | | |
|---|---|---|---|
| 1,824,516 | 9/1931 | Tyvand | 128/346 |
| 3,547,121 | 12/1970 | Cherry | 604/116 |
| 3,633,567 | 1/1972 | Sarnoff | 128/DIG. 15 |
| 3,786,805 | 1/1974 | Tourin | 128/87 R |
| 3,972,321 | 8/1976 | Proctor | 128/DIG. 26 |
| 4,180,058 | 12/1979 | Brem | 128/329 R |
| 4,228,796 | 10/1980 | Gardiner | 604/116 |
| 4,314,568 | 2/1982 | Loving | 604/116 |
| 4,362,157 | 12/1982 | Keeth | 604/116 |
| 4,485,808 | 12/1984 | Hepburn | 128/87 R |
| 4,489,716 | 12/1984 | Blackwood et al. | 128/87 R |

OTHER PUBLICATIONS

*The Journal of Bone and Joint Surgery*, vol. 37A, No. 6, 12/55.

*Primary Examiner*—C. Fred Rosenbaum
*Assistant Examiner*—Mark Rooney
*Attorney, Agent, or Firm*—Jacob Trachtman

[57] ABSTRACT

Position locating device for interstitial radiotherapy of a body portion comprising a flexible sheet member for being received about and conformed with a body portion which is to receive radiotherapy, the sheet member having a plurality of spaced position locating means, and attachment means for releaseably securing the sheet member about the body portion. The position locating means of the sheet member comprises a plurality of spaced openings arranged in rows and columns, and the attachment means comprises a pair of clamping units securing a plurality of bands with the ends of the sheet member. The clamping units are detachably secured with the sheet member for being replaced and repositioned therewith and the first ends of the bands are pivotally secured with the respective clamping units, while the second ends of each of the bands of one of the clamping units is detachably securable with a corresponding one of the second ends of the bands of the other clamping unit. The method comprises positioning a flexible sheet member having a plurality of spaced openings over a body portion which is to receive interstitial radiotherapy, conforming the sheet member with the surface of the body portion and securing its position thereon, marking the locations of selected openings of the sheet member onto the surface of the body portion, and thereafter removing the sheet member from the body portion.

5 Claims, 6 Drawing Figures

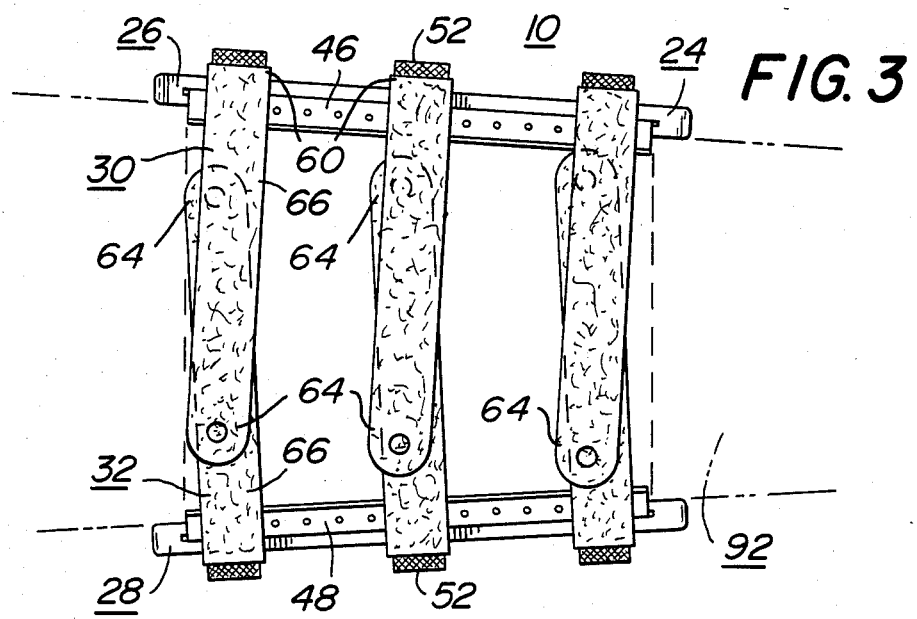
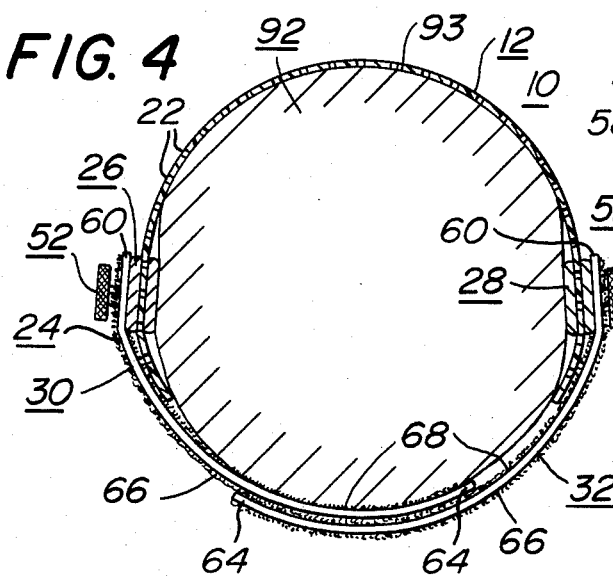
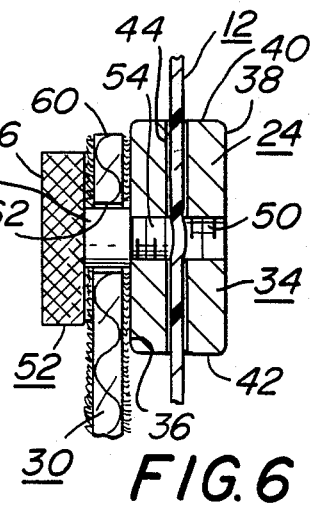
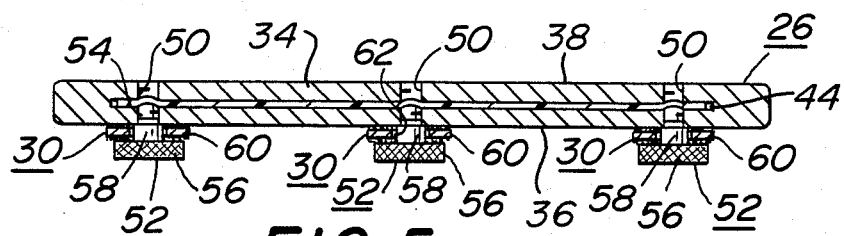

POSITION LOCATING DEVICE AND METHOD FOR INTERSTITIAL RADIOTHERAPY

BACKGROUND OF THE INVENTION

The present invention relates to a position locating device for use in radiotherapy, and more particularly to a device for locating on the surface of a body portion the points of entry and exit of hollow stainless steel needles for interstitial implantation of radioactive materials.

The interstitial implantation of radioactive isotopes is a well established technique for the treatment of malignant tumors. Short lengths of a radioactive source, such as Iridium-192, are linearly arranged within thin walled plastic tubes to form "ribbons." These ribbons are used as temporary interstitial implants in a wide variety of clinical situations. Each ribbon, which is very flexible, must be inserted into the body with the aid of a rigid trocar, in the form of a hollow stainless steel needle, which is sharpened at one end for piercing the skin and tumor bearing tissue. An array of the hollow needles are first inserted into the tissues to be implanted. The needles are typically spaced evenly throughout the volume of tissue to be irradiated, and are parallel to one another to avoid areas of underdose or overdose. After the hollow needles have been inserted, ribbons of radioactive sources are inserted into the bores of the needles to positions determined by the location of the tumor bearing tissue. In certain clinical situations the needles may be left in place in the body, along with the sources, for the duration of the implant, after which both are removed. In other situations, the needles may be pulled out of the body, leaving behind only the ribbon sources for the duration of the implant.

The clinical applications of the present invention relate to the implantation of such needles, which may also be pushed through the tissue and thereafter removed, leaving behind the ribbons of sources for the duration of the implant. The ribbons are typically anchored in place by crimping each of their free ends with a small metal disk or "button." When the desired radiation dose has been delivered, each ribbon is removed from the body by cutting off the button at one end and pulling the ribbon, by its opposite end, out through the skin. The classic technique for implantation of radioactive materials through soft tissue is illustrated and described on page 89 in connection with FIGS. 1-72 of the "Textbook of Radiotherapy," Third Edition, 1980, published by Lea & Febiger, Philadelphia, Pennsylvania.

In interstitial radiotheraphy, precision in the placement of the radioactive sources is important to the success of the treatment. Because of the limited volumes of the tissues being irradiated, and the rapid change in the intensity of radiation over small increments of distance from the sources, imprecise placement of the radioactive sources can result in areas which are subjected to underdoses and areas which are subjected to overdoses of radiation. Interstitial implants in the peripheral soft tissues of the body, such as in the extremities, are commonly arranged to provide one or more planes of radioactive sources. Each plane consists of multiple ribbons of sources which should be equidistant from one another and parallel. The key to obtaining planes of equally spaced and parallel ribbons of sources is to accurately locate the positions of the entry and exit points for the needles on the surface of the skin. This will determine the ultimate positions of the sources within the body. In the prior art, this position locating was performed by a free-hand method, using a ruler to mark out a row of equally spaced entry points on the skin on one side of the body. A row of exit points were then similarly marked on the opposite side of the body, while using visual sighting to try to keep the points of both rows in register in order to form a plane at the desired depth within the body. At best, the free-hand method is only an approximation, and can result in uneven spacing and non parallelism of the ribbons of sources and the planes formed by them. It is therefore desirable to provide an alternative to the free-hand method of locating the positions of the entry and exit points, especially on a body surface of non-uniform curvature, which may require modification in the placement of the entry and exit points to take into account continuous variations in the curvature of the body portion being implanted.

SUMMARY OF THE INVENTION

Accordingly, a principal object of the invention is to provide a new and improved position locating device and method for interstitial radiotherapy which overcome the deficiencies of the means and methods previously employed.

Another object of the invention is to provide a new and improved position locating device and method for interstitial radiotherapy which permits accurately locating the positions of corresponding entry and exit points on the surface at opposite sides of a body of either uniform or non-uniform curvature.

Another object of the invention is to provide a new and improved position locating device and method for interstitial radiotherapy which permits the accurate implantation of a series of hollow needles passing through pairs of corresponding entry and exit points so as to be parallel to one another and within the same plane, and which also provides entry and exit points for positioning needles in multiple parallel planes.

A further object of the invention is to provide a new and improved position locating device and method for interstitial radiotherapy utilizing a flexible template member for being positioned and conformed to a body surface having a curvature which is continuously changing over the region to be implanted.

A further object of the invention is to provide a new and improved position locating device and method for interstitial radiotherapy having components which may be used interchangeably and reversibly, and a flexible template member with opposite surfaces either of which can contact the body for simplifying the assembly and use of the device.

A further object of the invention is to provide a new and improved position locating device and method for interstitial radiotherapy which is of simple design and construction, permitting ease of assembly, disassembly, cleaning and sterilization for each use.

The above objects as well as many other objects and advantages of the invention are achieved by providing a position locating device for interstitial radiotherapy comprising a flexible sheet member for being received about and conformed with a body portion which is to receive radiotherapy, and attachment means for releaseably securing the sheet member about the body portion. The sheet member has a plurality of spaced position locating means such as a plurality of spaced openings forming a template. The sheet member may be made of a thin plastic material with the spaced openings arranged in rows and columns. The attachment means comprises first and second clamping units each secured with the sheet member proximate to a respective one of its ends, and a plurality of bands each having a first end secured with a respective one of the clamping units and second end which is detachably securable with the second end of a corresponding band of the other clamping unit for releaseably securing the sheet member about the body portion. The first ends of the bands may be pivotally secured with their respective clamping units for allowing their angular adjustment and may be provided with microhook attachment means for detachably securing together the second ends of corresponding bands. The flexible sheet member may include a centering means for positioning the sheet member on the body portion so that corresponding openings are located above and below the centering means. This assists in locating on the surface of the body portion the entrance and exit points of hollow stainless steel needles which are to be received into the body so that they extend through the tumor bearing tissue to be treated by the interstitial implantation of radioactive materials.

The method of the invention locates entrance and exit sites for hollow needles on the surface of a body portion which is to receive interstitial radiotherapy and includes positioning a flexible sheet member having a plurality of spaced openings over a body portion which is to receive interstitial radiotherapy, conforming the sheet member with the surface of the body portion and securing its position thereon, marking the locations of selected openings of the sheet member on the surface of the body portion, and removing the sheet member from the body. The selected locations of the openings of the sheet member are marked onto the surface of the body by inserting the end of a marking instrument, such as a surgical marking pen through selected openings of the sheet member. The method may also include defining a center line on the surface of the body portion partitioning the region which is to receive interstitial radiotherapy and positioning the sheet member over the body member for providing corresponding openings above and below the center line.

DESCRIPTION OF THE DRAWING

The foregoing and other objects and advantages of the invention will become more apparent as the following detailed description is read in conjunction with the drawing, in which:

FIG. 3 is an enlarged bottom plan view of the device shown in FIG. 1 after being applied about a body portion, FIG. 4 is an enlarged sectional view taken on line 4—4 of the device shown in FIG. 1 after being applied about a body portion, FIG. 5 is an enlarged sectional view taken on the line 5—5 of FIG. 1, and FIG. 6 is an enlarged sectional view taken on line 6—6 of FIG. 1.

Like reference numerals designate like parts throughout the several views.

DETAILED DESCRIPTION OF THE INVENTION

Figures 1, 2:
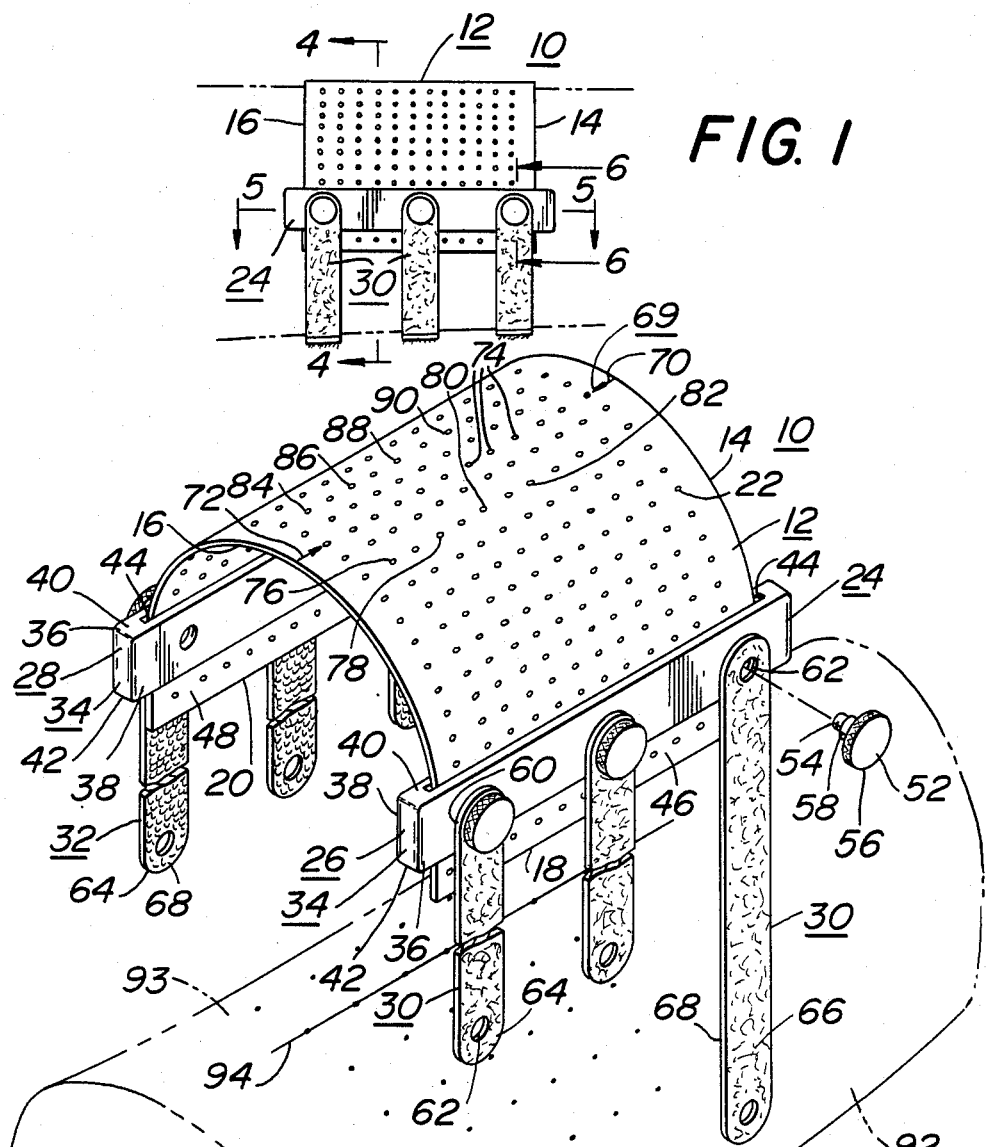
FIG. 1 is a side elevational view of a position locating device for interstitial radiotherapy embodying the invention.
FIG. 2 is an enlarged perspective view with parts broken away and exploded of the device shown in FIG. 1.

Refer to the figures which illustrate a position locating device 10 for interstitial radiotherapy embodying the invention. The device 10 comprises a flexible sheet member 12 which may be made of a thin plastic material such as polyethylene. The sheet member 12 may be of substantially rectangular form providing side edges 14 and 16 and end edges 18 and 20. The sheet member 12 is provided with a plurality of spaced position locating means such as the openings 22 which are arranged in rows and columns respectively parallel to the end edges 18 and 20 and the side edges 14 and 16. The openings 22 are of sufficient size to allow the insertion therethrough of the end of a marking instrument such as a surgical marking pen to provide a template for marking the skin of a body portion which is to receive radiotherapy.

Attachment means 24 comprises a pair of clamping units 26, 28 and a plurality of securing bands 30 and 32 respectively associated therewith. The clamping units 26, 28 each comprise a rectangular bar 34 with flat inner and outer surfaces 36 and 38 and top and bottom surfaces 40, 42. Each bar 34 has a slot 44 extending through its top and bottom surfaces 40 and 42 for respectively receiving an end portion 46, 48 of the sheet member 12 therethrough. Each bar 34 is also provided with a plurality of threaded openings 50 which extend between the outer and inner surfaces 36, 38 as shown in FIGS. 5 and 6. A plurality of fastening screws 52 each have a threaded end portion 54 received in one side of each of the openings 50, and are provided at the other end with a knurled knob 56. Each fastening screw 52 also has a neck portion 58 of an intermediate diameter joining the threaded portion 54 and knob 56 to form a spacer about which is received an end 60 of the bands 30 and 32. The bands 30 and 32 are provided with openings 62 at each of their ends 60 and 64 for having an end 60 received about the spacer provided by the neck portion 58 for being retained by a respective fastening screw 52.

The bands 30 and 32 may be provided with detachable securing means in the form of microhooks and microloops for attaching the distal ends 64 of the bands 30 of the clamping unit 26 with corresponding distal ends 64 of the bands 32 associated with the clamping unit 28. For this purpose the flat outer surfaces 66 of the bands 30 and 32 may be provided with microhook material while the opposite inner facing surfaces 68 have microloops, or vice versa.

The flexible sheet member 12 provides a template for marking the skin of a body portion about which it is secured by the attachment means 24. To assist in positioning the sheet member 12 so that it is properly centered over the region which is to receive radiotherapy, centering means 69 such as the indicating arrows 70 and 72 in alignment with a central row of openings 74 maybe utilized or any other such indicating means or line may be used. Openings 22 such as the opening 76, 78, 80, 82 below the center row of openings 74 may be selected corresponding to respective openings 84, 86, 88 and 90 above the row 74, so that each pair indicates an entrance point and an exit point for each needle which is to be inserted into the body portion which is to be treated. Of course any series of locations may be selected for such insertions of needles as may be required for providing the desired treatment in which needles are implanted in parallel relationship to each other and in planes which are spaced as required.

The assembly and disassembly of the components of the position locating means 10 is readily accomplished for providing the device 10 with the configuration, size or arrangement of openings 22 which are suitable for the required application. Thus, for a particular application a flexible sheet member 12 is chosen having a desired pattern of openings 22 with the required spacing of openings for allowing selection of the desired arrangement for the implanting of needles in the body portion. Each of the ends 18 and 20 of the sheet member 12 may be inserted through the slot 44 of its respective clamping units 26, 28 and each clamping units 26, 28 may be positioned the desired distance apart and preferably parallel to the rows of openings 22 depending upon the surface to be covered. The fastening screws 52 which may have already been inserted in the openings 50 and through the opening 62 of each of the ends of the bands 30 and 32 which are chosen to be of appropriate length for the application, are now tightened so that they impinge upon and clamp the end portions 46, 48 of the sheet member 12 with the bars 34. When required, the attachment means 24 are readily disassembled from the sheet member 12 by loosening the fastening screws 52. The removal of the fastening screws 52 also allows the replacement of the bands 30 and 32 when this is desirable. The symmetrical arrangement of the bars allows them to be used interchangeably and reversibly, thus increasing the versatility and usefulness of the position locating device 10.

In the application of the position locating device 10 to a body extremity, such as the body portion 92, which is to be treated, a center line 94 is located or noted on the body 92 partitioning the region which is to receive interstitial radiotherapy (See FIG. 2). The flexible sheet member 12 is then positioned over the skin or surface 93 of the body 92 and preferably centered by aligning the arrows 70, 72 or the row 74 of openings of the centering means 69 over the center line 94. This provides, for example, a plurality of openings 76, 78, 80, 82 below the line 74 corresponding to openings 84, 86, 88, 90 thereabove. With the sheet member 12, thus positioned, it is secured about the body 92 with the bands 30, 32, so that their ends 64 associated with the clamping unit 26 engage corresponding ends 64 of the bands 32 associated with the clamping unit 28. FIG. 3 illustrates the manner in which the bands 30 and 32 are attached to each other so that the member 12 is securely positioned and conformed to the surface 93 of the body 92 as also shown in FIG. 4. Thus, the flexible sheet member 12 by the force applied by the bands being secured to each other, can be drawn over and conformed with surfaces of continuously varying curvature such as the surfaces of an extremity of the body which is to receive the interstitial radiotherapy. FIG. 3 also illustrates the angular relationship between the bands 30, 32 due to the taper of the body portion 92 which angular relationship will vary depending upon the degree of tapering. Such angular adjustment of the bands 30 and 32 is readily achieved by the pivotal connection of their ends 60 with the fastening screws 52.

With the position locating device 10 applied to a body portion in the proper position and conformed therewith, the flexible sheet member 12 is used as a template by which selected openings above and below the centering means 69 are marked as by inserting the point of a surgical marking pen through openings such as 76, 78, 80, 82, 84, 86, 88, 90 or any other arrangement or selection of openings 22 to provide marks on the skin or surface 93 of the body portion 92 designating sites for entrance and exit of hollow needles which are to be implanted in the tumor bearing region of the body. After the appropriate selected marks have been made, the position locating device 10 is removed by detaching the ends 64 of the bands 30 and 32. With the marks clearly visible and accessible, the steel needles may now be implanted as required for interstitial radiotherapy.

The components of the position locating device 10 may be replaced or readjusted for subsequent position locating operations which may require different templates or spacings of the clamping units and/or lengths of bands for applying same to a body portion. As previously noted such replacement or readjustment of components may readily and easily be achieved by loosening or removing the fastening screws 52.

It will be obvious to those skilled in the art that additional forms and variations of the disclosed position locating means will be readily apparent to those skilled in the art, and that the invention may find wide application with appropriate modification to meet the particular requirements and circumstances, but without substantially departing from the essence of the invention.

What is claimed is:

1. A position locating device for interstitial radiotherapy of a body portion comprising a flexible sheet member for being received about and conformed with a body portion which is to receive radiotherapy, the sheet member having a plurality of spaced position locating means and first and second opposite ends, and attachment means for releasably securing the sheet member about the body portion comprising joining means securing a plurality of bands with the sheet member, the joining means providing first and second clamping units each detachably secured with the sheet member proximate to a respective one of its ends for being replaced and repositioned therewith, the plurality of bands comprise first and second sets having first ends pivotably secured with a respective one of the first and second clamping units for allowing their angular adjustment with the second ends of the first set of bands being detachably securable with the second ends of the second set of bands for releasably securing the sheet member about the body portion, and each of the clamping units comprises a flat bar having a slot for receiving therethrough an end of the sheet member and a plurality of screw elements threadedly engaging a respective one of the bars for clamping and securing the sheet member therewith, and the first ends of the bands have an opening for receiving a respective screw element therethrough for securing same with the bar unit and allowing pivotal movement thereabout.

2. The position locating device of claim 1 in which the bands are flat strips of flexible material provided with microhook attachment means for detachably securing the second ends of the first set of bands with the second ends of the second set of bands.

3. The position locating device of claim 1 in which the position locating means of the sheet member comprises a plurality of spaced openings.

4. The position locating device of claim 1 in which the sheet means is of a plastic material.

5. The position locating device of claim 1 in which the position locating means of the sheet member comprises a plurality of spaced openings, the sheet means is of plastic material and the spaced openings are arranged in rows and columns.

* * * * *